United States Patent [19]

Igarashi et al.

[11] Patent Number: 5,248,824

[45] Date of Patent: Sep. 28, 1993

[54] METHOD OF PREPARING N,N,N-TRIMETHYLSPHINGOSINE

[75] Inventors: Yasuyuki Igarashi; Mahammad N. Ahmad; Hirofumi Okoshi, all of Seattle; Sen-Itiroh Hakomori, Mercer Island, all of Wash.

[73] Assignee: The Biomembrane Institute, Seattle, Wash.

[21] Appl. No.: 879,332

[22] Filed: May 7, 1992

Related U.S. Application Data

[62] Division of Ser. No. 636,353, Dec. 31, 1990, Pat. No. 5,137,919.

[51] Int. Cl.$^5$ ............................................. C07C 209/00
[52] U.S. Cl. ..................................... 564/292; 564/507
[58] Field of Search ................................. 564/292, 507

[56] References Cited

U.S. PATENT DOCUMENTS 3,755,334  8/1973  Sommer ........................... 564/292 X

OTHER PUBLICATIONS

Hannun and Bell, "Lysosphingolipids Inhibit Protein Kinase C: Implications for the Sphingolipidoses," *Science*, 235: 670–674 (Feb. 6, 1987).

Igarashi et al., "A Specific Enhancing Effect of N,N,-Dimethylsphingosine on Epidermal Growth Factor Receptor Autophosphorylation," *J. Biol. Chem.*, 265 (10): 5385–5389 (1990).

Sommer et al., "Alkylation of Amines. A General Exhaustive Alkylation Method for the Synthesis of Quaternary Ammonium Compounds," *J. Org. Chem.*, 36 (6): 824–828 (1971).

Igarashi et al., "Effect of Chemically Well-Defined Sphingosine and Its N-Methyl Derivatives on Protein Kinase C and src Kinase Activities," *Biochem.*, 28: 6796–6800 (1989).

*Primary Examiner*—Richard L. Raymond
*Attorney, Agent, or Firm*—Sughrue, Mion, Zinn, Macpeak & Seas

[57] ABSTRACT

The invention relates to a novel compound, compositions and medicaments thereof and a method of inhibiting cell proliferation, platelet aggregation (induced by various factors), and inhibiting malignant phenotypes of tumor cells such as those having a metastatic property, using said compound, composition or medicament. N,N,N-trimethylsphingosine shows superior cell proliferation inhibitory and anti-metastatic activity over related compounds.

2 Claims, 11 Drawing Sheets

Sphingosine (1) X=H
N,N-Dimethylsphingosine (2) X=Me

N,N,N-Trimethylsphingosine (3)

METHOD OF PREPARING N,N,N-TRIMETHYLSPHINGOSINE

This is a division of application Ser. No. 07/636,353 filed Dec. 31, 1990 now U.S. Pat. No. 5,137,919.

FIELD OF THE INVENTION

The invention relates to compounds with a profound effect on protein kinase C activity and mammalian cell proliferation; and methods of using the same.

BACKGROUND OF THE INVENTION

Sphingosine (SPN) is a long chain unsaturated amino alcohol of the formula $C_{18}H_{37}O_2N$ found in cell membranes and in high concentration in nervous tissue. Sphingosine and sphingoid base (a long chain aliphatic base comprising a 1,3-dehydroxy-2-amino group at a terminus and derivatives thereof) have been implicated as inhibitors of protein kinase-C (PK-C) and EGF receptor-associated tyrosine kinase (EGF-RK) (Hannun & Bell, Science, 235, 670, 1987; Hannun, JBC, 261, 12604, 1986; Kreutter et al., JBC, 262, 1632, 1987).

Protein kinase-C activity is related closely to cell growth and recent studies indicate that increased tumorigenicity is correlated with over expression of PK-$C_{\beta1}$ and PK-$C_\gamma$ in some experimental tumors (Housey et al., Cell, 52, 343, 1988; Persons et al., Cell, 52, 447, 1988). A mutant PK-$C_6$ induces highly malignant tumor cells with increased metastatic potential (Megidish Mazurek, Nature, 324, 807, 1989). It would appear that aberrant expression of PK-C may relate to tumor progression.

Recent studies indicate that phospholipids, sphingolipids and metabolic products thereof have an important role in the modulation of transmembrane signaling through PK-C and other membrane-associated kinases, such as EGF receptor-associated tyrosine kinase (Hakomori, JBC, 265, 18713, 1990). For example, PK-C activity is promoted by diacyl glycerol and inhibited by sphingosine (Hannun & Bell, supra; Hannun & Bell, Science, 243, 500, 1989; Merrill & Stevens, Biochim Biophys Acta, 1010, 131, 1989).

Sphingosine did not inhibit PK-C in vitro or at concentrations below 100 μM and did not exhibit a stereospecific effect on PK-C (Igarashi et al., Biochem, 28, 6796, 1989). Many of the studies described above employed sphingosine obtained from a commercial source (for example Sigma Chemical Company) and the preparations contained various impurities including 3-O-methylsphingosine, 5-O-methylphingosine and N-methylsphingosine. The impurities are likely to result from the process of preparation, namely methanolysis of sphingomyelin or cerebroside. Furthermore, in the sphingosine backbone, the D-erythro configuration about the chiral carbons is often converted to the D-threo configuration.

Igarashi et al. (supra) found that the inhibitory effect of sphingosine on PK-C activity is due to: (1) the stereospecific configuration of C1 to C3 (D-erythro configuration required); (2) presence of a long-chain aliphatic group-, and (3) perhaps most essential, a negative charge at the primary amino group at C2. If the amino group was N-acetylated, the PK-C inhibitory activity was abolished since the negative charge of an amino group was eliminated by acetylation. However if the anionic character of the amino groups was enhanced by N-methylation, the stereospecific PK-C inhibitory activity was enhanced.

SUMMARY OF THE INVENTION

One object of the invention is to provide a compound and composition for inhibiting metastatic properties of malignant tumor cells, for controlling cell proliferation and for treating various disorders characterized by abnormal cell proliferation.

Another object of the invention is to provide a compound and composition which inhibits protein kinase-C.

A further object of the invention is to provide a compound and composition for inhibiting platelet aggregation.

A fourth object of the invention is to provide a compound and composition for inhibiting inflammation.

Another object of the invention is to provide a method for making N,N,N-trimethylaphingosine.

A sixth object of the invention is to provide a medicament and method of treating malignancy and inhibiting metastatic properties of malignant tumor cells.

These and other objects have been attained by the development of a method for making N,N,N-trimethylaphingosine and observations in vitro and in vivo of its efficacy in controlling cell proliferation, and inhibiting malignant phenotypes of tumor cells.

It has been found that N,N,N-trimethylsphingosine has a higher inhibitory activity on protein kinase-C and metastatic potential of tumor cells than other sphingosine derivatives; inhibits platelet aggregation and tumor-induced platelet interaction; inhibits inflammatory processes; and is water soluble. A striking depression of tumor cell metastasis by N,N,N-trimethylsphingosine could be due to its inhibitory activity on protein kinase-C or on platelet aggregation or on both.

BRIEF DESCRIPTION OF THE DRAWINGS

In FIG. 2A the growth of human colonic cancer cell line COLO-205 was monitored. In FIG. 2B the growth of human lung cancer cell line LU-65 was monitored. In FIG. 2C the growth of human gastric cancer cell line MKN-74 was monitored. In each Figure the ordinate represents the percent inhibition of tritiated thymidine incorporation, the solid circles represent sphingosine, the open circles represent N,N-dimethylsphingosine and the triangles represent N,N,N-trimethylsphingosine.

FIG. 3 depicts the comparative effect of various reagents on tumor cell differentiation. MKN-74 cells were exposed to N,N,N-trimethylsphingosine (open squares), N,N-dimethylsphingosine (open circles), 8-chloro-cyclic AMP (open triangles), dibutyryl cyclic AMP (solid triangles), sphingosine (solid circles) and hexamethylenebisacetamide (solid squares).

In FIG. 4A the ordinate shows the amount of $^{32}P$-ATP that was incorporated into myelin basic protein. In FIG. 4B radioactive incorporation into histone III-S is depicted on the ordinate. In both panels SP represents sphingosine, MMS represents N-monomethylsphingosine, DMS represents N,N-dimethylsphingosine and TMS represents N,N,N-trimethylaphingosine.

In FIG. 6A the open bars depict the total number of lung colony deposits; the stippled bars depict the number of lung colonies with a diameter of greater than 1 mm; and the solid bars depict the number of lung colonies with a diameter of less than 1 mm. Bars 1-3 depict the number of deposits observed 14 days after injection. Bars 4-6 depict the number of lung colony deposits in animals that received BL6 cells and 1 minute later received 0.2 mg of N,N,N-trimethylsphingosine (TMS). Bars 7-9 depict the number of lung colony deposits in animals that received BL6 cells and 0.2 mg of TMS simultaneously. Bars 10-12 depict the number of deposits in animals that received TMS three hours after administration of BL6.

In FIG. 6B the number of lung colonies was determined 16 days after treatment, the treatment consisting of varying doses and routes of administration. Bar 1: $3 \times 10^4$ BL6 cells i.v. Bar 2: $5 \times 10^6$ BL6 cells s.c. Bar 3: $3 \times 10^4$ BL6 cells i.v. with 0.5 mg TMS i.p. one hour later. Bar 4: $5 \times 10^6$ BL6 cells s.c. with 0.5 mg sphingosine i.v. one hour later. Bar 5: $5 \times 10^6$ BL6 cells s.c. with three doses of 0.5 mg TMS i.v. 2, 3 and 4 days later.

In FIG. 6C the dose responsiveness of BL6 metastatic potential to TMS is presented. Bar I depicts a control comprising colony numbers in lungs of animals wherein $4 \times 10^4$ BL6 cells in PBS were injected i.v. Bar 2 depicts the number of colonies in lungs of animals that received 0.1 mg of TMS in 100 $\mu$l PBS, 1 minute after injection of BL6 cells. Bar 3 represents animals treated in the same manner except that the dose of TMS was doubled to 0.2 mg. Bar 4 represents animals that were treated similarly but with 0.5 mg of TMS. Bar 5 represents animals that first were injected with 0.5 mg of TMS in PBS and 1 minute later were injected with $4 \times 10^4$ BL6 cells in 100 $\mu$l of PBS. Sixteen days after treatment, the mice were sacrificed, lungs opened and the number of colonies in the lungs were counted under a dissecting microscope.

FIGS. 7A and 7B depict the effect of N,N,N-trimethylsphingosine (TMS) on platelet aggregation. A 0.45 ml aliquot of human platelet suspension ($3-5 \times 10^5$ platelets per $\mu$l of Tyrode's buffer) was incubated with sphingosine or TMS for 2 minutes. Then platelet aggregation was induced by the addition of either $\gamma$-thrombin (FIG. 7A) or adenosine diphosphate (ADP) (FIG. 7B) in 0.05 ml. The degree of aggregation was determined in an aggregometer and the data analyzed with an integrated computer (Kyoto Daiichi Kagaku Co. Ltd.).

FIG. 9 depicts the inhibition of T-thrombin-induced phosphorylation of 40 kD protein of human platelets by sphingosine and TMS. Human platelets ($3 \times 10^5/\mu$l) were prelabeled with $^{32}$P-phosphoric acid (0.2 mci/ml) in Tyrode's buffer containing 22 mM trisodium citrate, 1 mg/ml glucose and 3.5 mg/ml bovine serum albumin (pH 6.5) for 75 minutes at 37° C. After centrifugation (600 $\times$ g, 10 minutes), the platelets were resuspended in Tyrode's buffer (pH 7.2), aliquoted in plastic tubes and preincubated at 37° C. for 5 minutes with various concentrations of sphingosine and its derivatives (added as 50% ethanol solutions with a final ethanol concentration of 0.5%). Platelets then were stimulated with thrombin (10 $\mu$M). The reactions were stopped after 30 seconds by the addition of 5 x sample buffer, the samples were boiled and loaded onto 10% SDS-polyacrylamide gels. The proteins were separated electrophotectically. Lane 1-control without stimulation by thrombin; Lane 2-stimulation by 1$\mu$ unit/ml of $\gamma$-thrombin; Lane 3-stimulated by thrombin but added with 1 $\mu$M TMS; Lane 4-stimulated by thrombin but added with 10 $\mu$M TMS; Lane 5-stimulated by thrombin but added with 20 $\mu$M TMS; Lane 6-stimulated by thrombin but added with 30 $\mu$M TMS; Lane 7-stimulated by thrombin but added with 20 $\mu$M sphingosine; Lane 8-stimulated by thrombin but added with 20 $\mu$M N,N-dimethylsphingosine.

DETAILED DESCRIPTION OF THE INVENTION

N,N,N-trimethylsphingosine (TMS) is highly water soluble, particularly at physiologic pH. Thus the compound has a distinct advantage over sphingosine, N-monomethylsphingosine and N,N-dimethylsphingosine, which are less water soluble, as a modulator of cell proliferation.

As used herein, sphingosine indicates sphingosine irrespective of D- or, L- or, erythro- or threo- configuration.

Further as used herein, "synthetically prepared" means a product prepared from commercially available reagents and building blocks and assembled into sphingosine and derivatives thereof by chemical reaction in vitro. Otherwise, sphingosines are prepared from sphingolipide which occur naturally.

Because of the multi-fuctionalized nature of the parent molecule, sphingosine, direct quaternization by exhaustive methylation (Sommer et al., J. Org. Chem. 36, 824, 1971) or reductive methylation using aqueous formaldehyde ($CH_2O/NAH_2PO_3$) is not always reproducible. Alternatively, N,N,N-trimethylsphingosine can be prepared synthetically from commercially available unsubstituted reagents. For example, it is found that unsubstituted sphingosine (Sigma Chemical Company) can be derivatized to form (4E)-N,N-dimethyl-D-erythro-sphingosine by a known method (Igarashi et al. JBC, 265, 5385, 1990). The N,N-dimethylsphingosine so obtained undergoes quaternization in almost quantitative yield.

Briefly, about a 37% aqueous solution of formaldehyde (which is about 20 eq.) is added to a solution of D-erythro-sphingenine in acetate buffer (NaOAc-AcOH-$H_2O$, pH 4.5). The solution is mixed at room temperature for about 10 minutes and then sodium cyanoborohydride ($NaBH_3$-CN) is added three times (at about 3.0, 2.0 and 1.0 eq., respectively). Excess methanol is added sequentially at five minute intervals. The solution is concentrated under a nitrogen stream in an "N-EVAP" (Organomation Assoc., Inc., South Berlin, Mass.) and the compound extracted with chloroform. When the quantity is large (that is more than about 5–10 mg), the solution is recommended to further concentration under reduced pressure in a rotary evaporator. The extract can be purified by high pressure thin layer chromatography using standard procedures. By that technique the compound has an $R_f$ of about 0.6 in a buffer comprising $CHCl_3:MEOH:NH_4OH$ in a ratio of 8:2:0.2 by volume. N,N-dimethylsphingosine prepared as described above was obtained as a colorless syrup in about 80% yield. The molecule has a formula weight of 329.3281 with a formula of $C_{20}H_{40}HNO_2$ as deduced from high resolution mass spectrometry.

Then about 30 milligrams (0.091 m/mol) of (4E)-N,N-dimethyl-D-erythro-sphingosine (DMS) are dissolved in about 1.5 ml of anhydrous chloroform. Freshly distilled iodomethane (a volume of about 170 μl, 2.73 m/mol) is added to the DMS solution and the mixture is stirred in the dark at ambient temperature. (The amount of excess iodomethane is not critical and amounts from 25 to 100% in excess produce satisfactory results.) The reaction generally is complete in a few hours, although for convenience the mixture is allowed to stand overnight. Progress of the reaction can be monitored by thin layer chromatography (TLC) using a buffer comprising ethyl acetate:methanol:ammonium hydroxide in a ratio of 20:10:2. After incubation, the precipitated quaternary ammonium salt is diluted with water and then repeatedly extracted with chloroform (3 ml×4). The organic layer is dried over magnesium sulphate and then concentrated in vacuo.

Practicing the above method, 37 mg (86% yield) of compound was obtained as yellow crystals.

The yellow crystals are dissolved with stirring in an aqueous suspension of preneutralized (pH=7.00) anion exchange resin (chloride form, Dowex 1×2-400, 500 mg) at room temperature for three hours. The mixture is then filtered through a sintered glass funnel and then freeze dried (8 millitorr for two days).

Practicing the above method, 26.5 mg (93% yield) of N,N,N-trimethylsphingosine chloride salt was obtained. The structure of the product was ascertained by proton nuclear magnetic resonance (500 MHz, $CDCl_3$) and found to contain nine hydrogen groups and a trimethyl derivatized amino group. $^1H$ NMR ($D_2O$) δ 0.88 (t, 3, J=6.8 Hz, Me), 1.31 (br s, 22, 11xCH_2), 2.08 (q, 2, J=6.8 Hz, 2xH-6), 3.29 (s, 9 N+Me_3), 3.38 (br s, 1, H-3), 4.13 (br s, 2, 2xH-1), 5.57 (dd, 1, J=3.1 and 3.4 Hz, H-4), and 5.90 (m, 1, H-5). The predicted molecular formula of the compound is $C_{21}H_{44}NO_2$ with an expected molecular weight of 342.3372 and mass spectroscopy revealed a formula weight of 342.3371 ($C_{21}H_{44}NO_2$, Δ-0.0003).

The effect of TMS on cell proliferation was demonstrated in part by exposing various tumor cells to the compound in vitro and in vivo. For comparison purposes those same test cells were also exposed to sphingosine and N,N-dimethylsphingosine. A ready advantage of TMS over the other two compounds is its water solubility. N,N-dimethylsphingosine and sphingosine are soluble in water as chloride salts and at slightly acidic pH. At neutral or physiologic pH, those solutions tend to form opaque suspensions. TMS is soluble under acidic, neutral or basic conditions providing stable, clear solutions.

An in vitro assay relying on tritiated thymidine incorporation was used to ascertain the effect of various compounds on cell proliferation. Briefly, tumor cells were seeded in flat bottom 96 well plates (Corning, N.Y.) at a concentration of $2 \times 10^4$ cells per well. The cells were cultured for 2 days in DMEM containing various concentrations of sphingoid which was added as a PBS solution. The medium was then supplemented with tritiated thymidine at a concentration of 0.5 μCi per well. Following a six hour incubation the cells were collected using the PHD Cell Harvester (Cambridge Technology, Cambridge, Mass.) and amounts of incorporated radioactivity were determined after adding a suitable cell lysing agent and scintillation cocktail, such as ScintiVerse BD (Fisher Scientific, Fairlawn, Calif.) which performs both functions. In the figures, the results are presented as the percent of cell growth inhibition relative to control cultures that were not exposed to a test substance.

Figure 1:
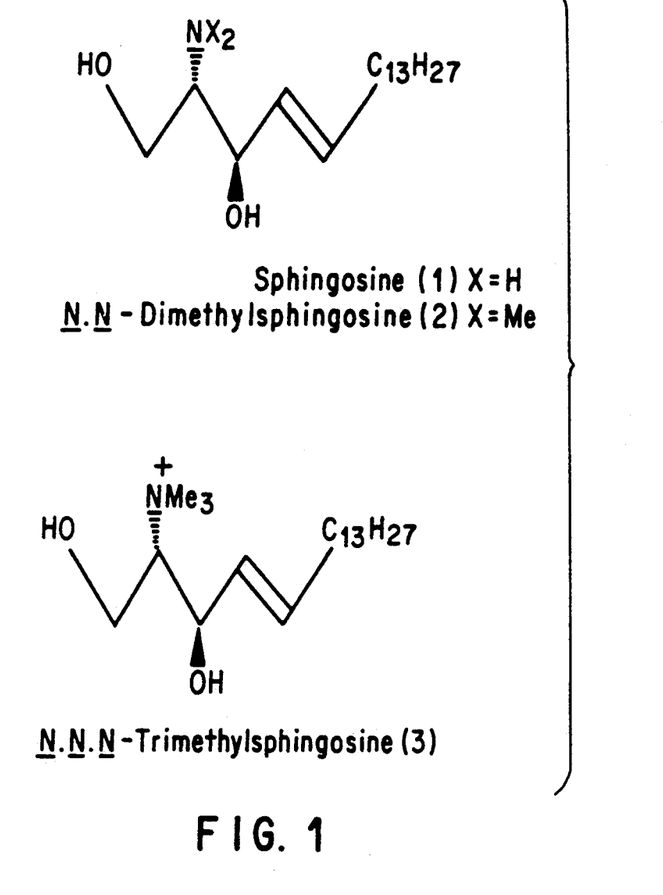
FIG. 1 depicts the structure of N,N,N-trimethylsphingosine and related compounds.
Figure 2A:
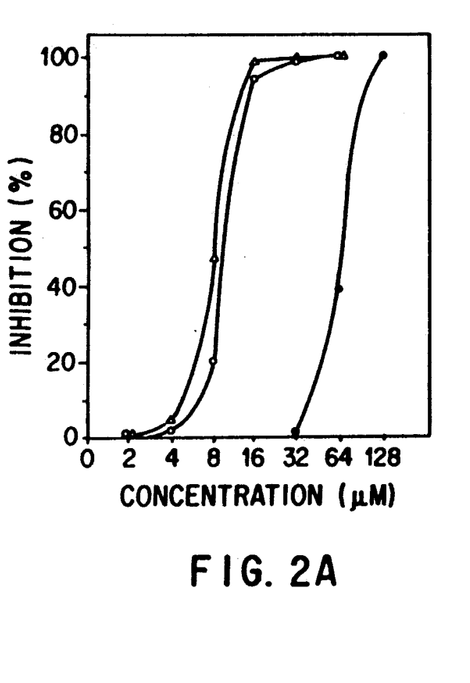
FIGS. 2A-2C show the effect of sphingosine derivatives on human tumor cell growth.
Figure 2B:
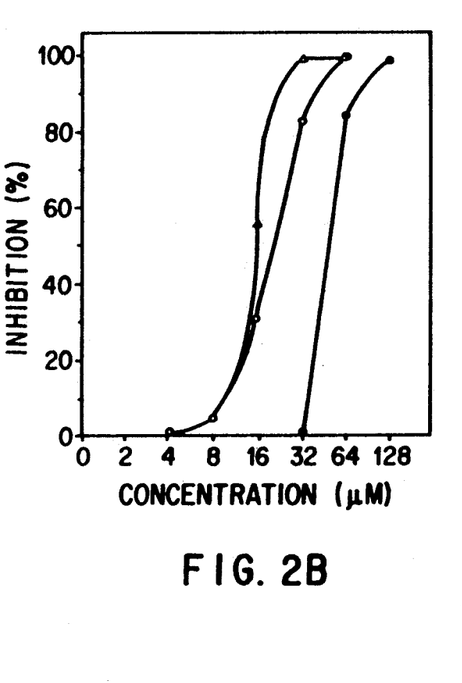
Figure 2C:
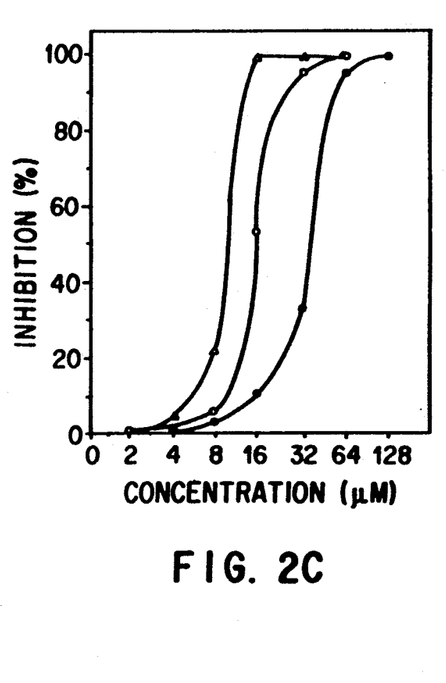

Three cancer cell lines were examined, COLO-205, a human colon cancer line (ATCC No. CCL 222); Lu-65, a lung cancer cell line (T. Yamada et al., Jpn. J. Cancer Res., 76, 967-976 (1985); and MKN-74, a gastric cancer cell line (Motoyama et al., Acta Med. Biol., 27, 49–63 (1979). As depicted in FIG. 2, in each case TMS was superior to sphingosine in the ability to inhibit tumor cell growth. TMS showed an advantage over DMS although not of the same magnitude. Nevertheless because of the increased efficacy of TMS over DMS, lower amounts were required to effect a specified level of inhibition.

Figure 3:
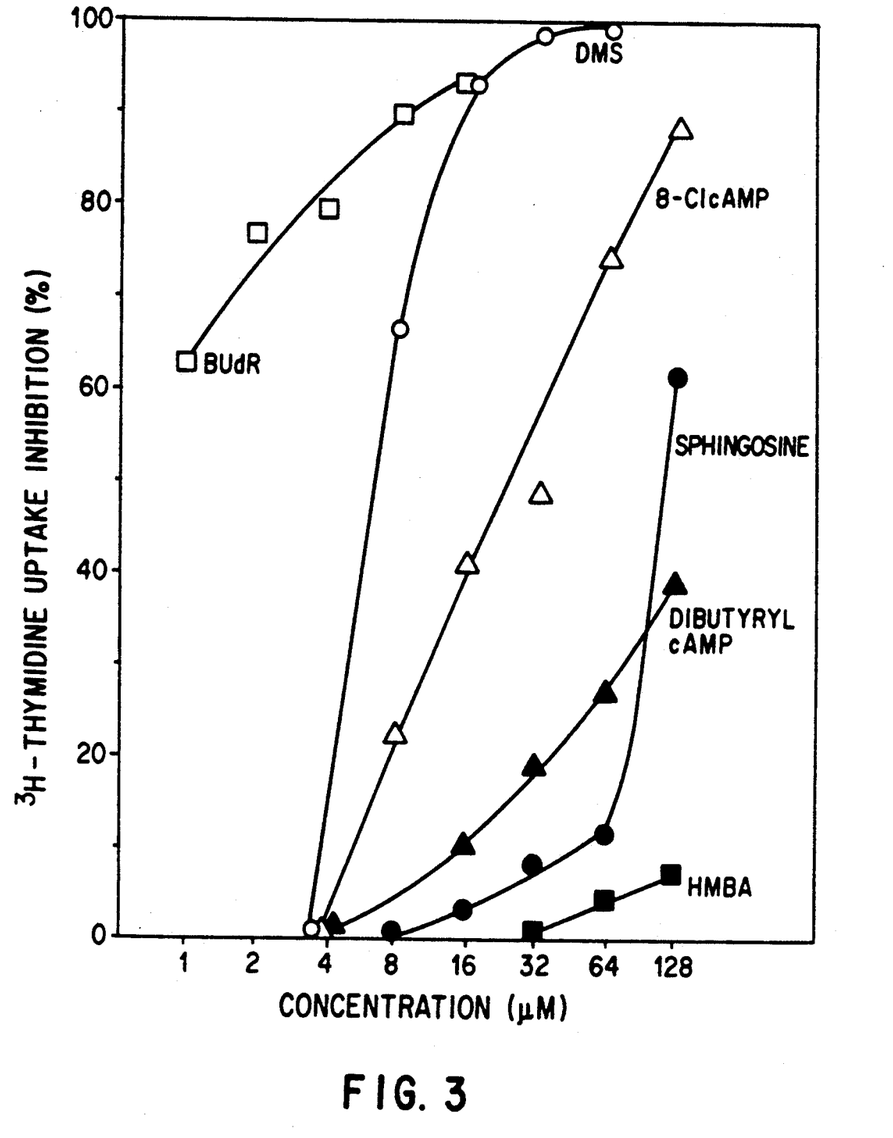

The enhanced inhibitory activity of TMS is validated in the data summarized in FIG. 3. MKN-74 cells were exposed to cAMP and derivatives thereof and to HMBA, which are known to inhibit tumor cell growth by differentiation induction. Clearly, TMS was the most effective inhibitor of tumor cell growth.

In another in vitro assay, the influence of various compounds on PK-C activity was monitored. Certain tumor cells present high levels of PK-C activity. The human epidermoid carcinoma cell line A-431 (ATCC No. CRL 1555) was used in a bioassay for PK-C activity as described in Igarashi et al. (supra). Briefly, phosphatidylserine (5 μg/tube) and 1,2-diolein (0.05 μg/tube), with or without an appropriate quantity of a sphingosine derivative sample, were added in an organic solvent, ethanol or ehtanol/chloroform, to a 1.5 ml tube (Sarstedt) and the mixture was evaporated under a $N_2$ stream. The lipid mixture was sonicated in about 30 μl of 20 mM Tris-HCl (pH 7.5) for 30 minutes. The resulting liposomes were supplemented with a buffer mixture comprising 25 mM Tris-HCl (pH 7.5), 10 mM $MgCl_2$, 400 μM EDTA, 50 μM EGTA, 500 μM $CaCl_2$, 200 μg/ml histone III-S or myelin basic protein and 20 μM δ[$^{32}P$]-ATP ($2 \times 10$ cpm) to a final volume of about 90 μl. The reaction was initiated by adding about 10 μl of PK-C, which was prepared from A431 cells as described in Igarashi et al. (supra) or from mouse brain as described in Kikkawa et al. (Biochem Biophys Res. Comm., 135, 636, 1986) and contained about 1–2 μg protein, and the mixture was incubated for ten minutes at 30° C. The reaction was terminated by the addition of 1 ml of a 1 mM ATP solution at pH 7.5 containing 25% TCA and 1% BSA. The precipitate was collected by centrifugation, washed twice with 1 ml of 25% TCA, then dissolved in 1 ml of 1M NAOH containing 0.1% deoxycholate with slight heating (80° C. for ten minutes) and counted in a scintillation counter. Reaction mixtures without phosphatidylserine, 1,2-diolein or $Ca^{2+}$ were used as controls.

Figure 4A:
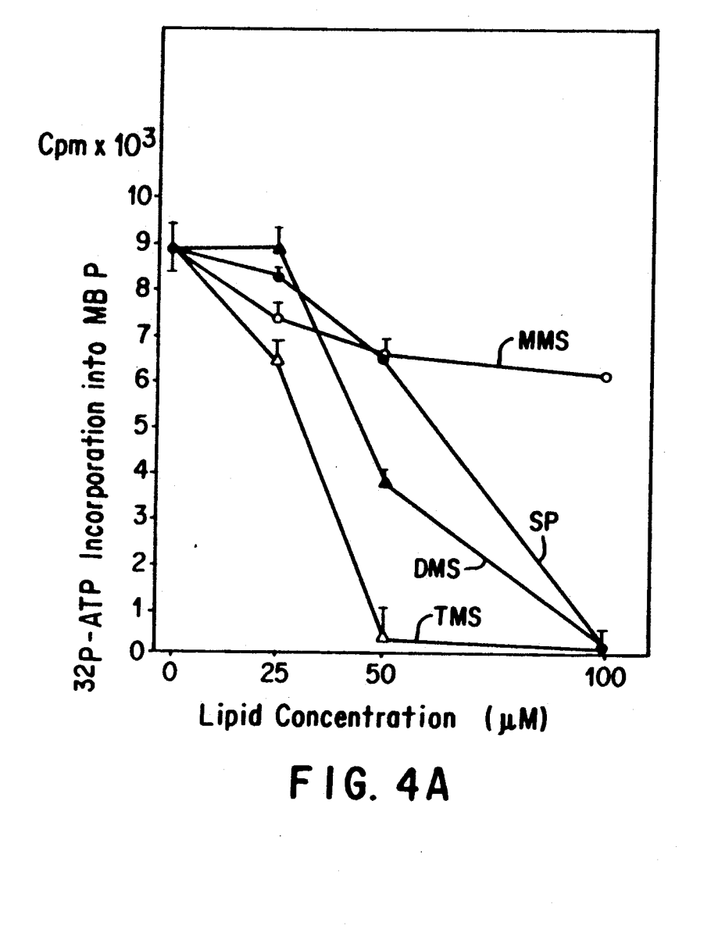
FIGS. 4A and 4B depict the effect of sphingosine derivatives on protein kinase-C activity in A431 cells. The standard liposome method of Kraft and Anderson (Nature 301, 621, 1983) was used.
Figure 4B:
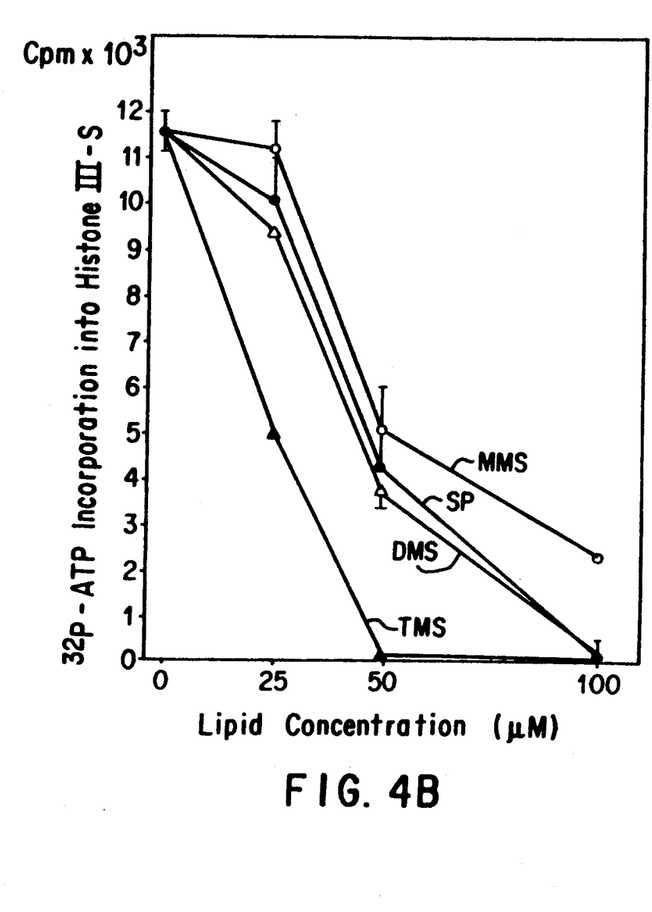

The bioassay used two different substrates, histone III-S and myelin basic protein. Data from a series of experiments are summarized in FIG. 4. Regardless of the substrate, TMS was superior to the other compounds in the ability to inhibit PK-C.

Figure 5A:
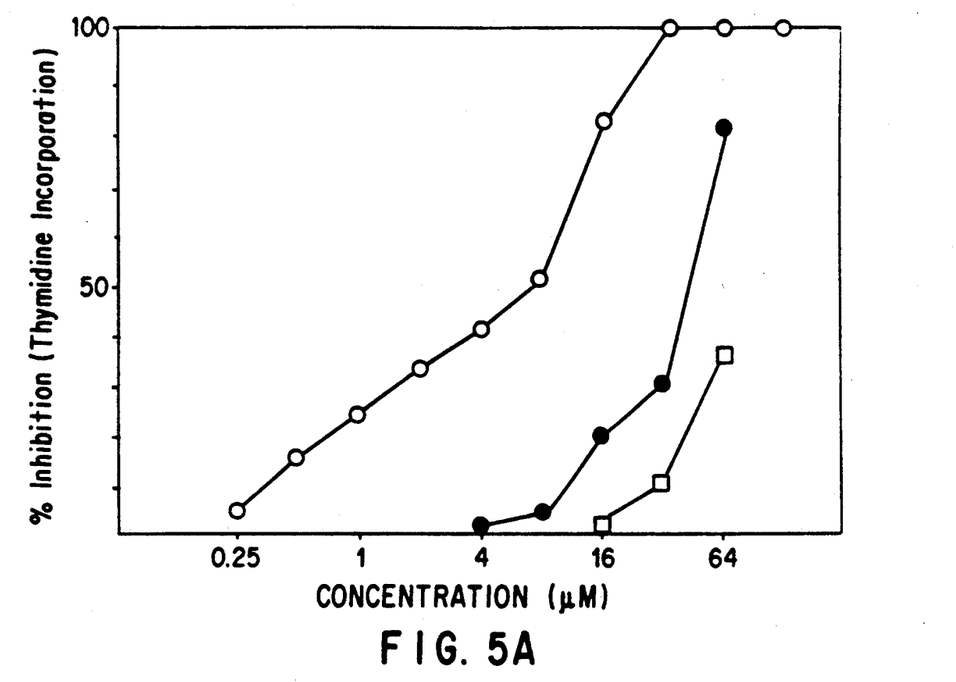
FIGS. 5A and 5B depict the effect of N,N,N-trimethylsphingosine (open circles), N,N-dimethylsphingosine (solid circles) and sphingosine (open squares) on two melanoma cells lines, BL6, a highly malignant cell line, in FIG. 5A and F1, a cell line of low malignancy, in FIG. 5B. Cell proliferation was evidenced by tritiated thymidine incorporation into DNA.
Figure 5B:
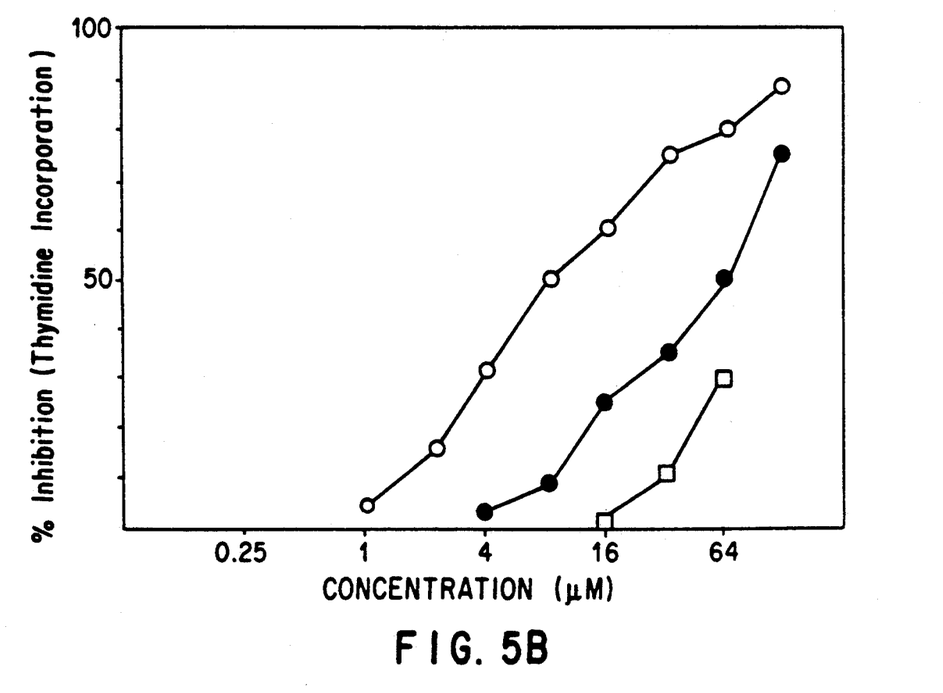

Although the data show a superior PK-C inhibitory activity of TMS over the remaining tested compounds, there are other advantages to TMS. Certain cancer cells show a higher metastatic potential and invasive capability than others. For example the BL6 and F10 melanoma cell lines are highly metastatic and invasive. On the other hand, the F1 variant is much less metastatic and invasive (I. R. Hart et al., Amer. J. Pathol, 97, 587-592 (1979); G. Poote et al., Cancer Res. 42, 2770-2778 (1982); F1 and F10 clones from ATCC CRL 6323, and CRL 6475, respectively). BL6 and F1 cells were tested in vitro as described above. As shown in FIG. 5 TMS was more effective than DMS and sphingosine at inhibiting cell growth. Also BL6 cells were more sensitive to TMS treatment as evidenced by the leftward shift of the TMS curve to lower concentrations.

Figure 6A:
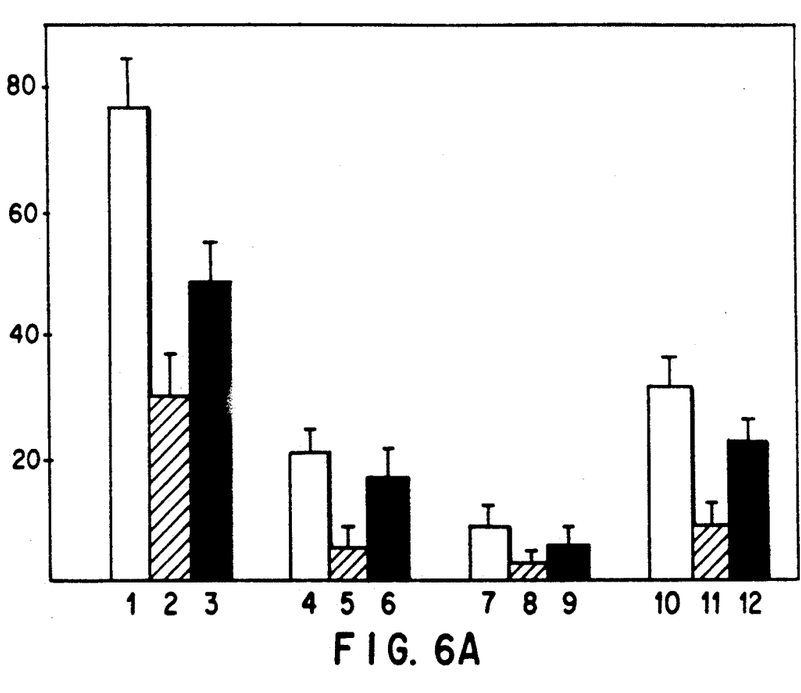
FIGS. 6A-C depict the effect of N,N,N-trimethylsphingosine on lung metastatic deposits after intravenous injection of BL6 cells into mice. Each graph represents the mean and standard deviation of results obtained in 8 animals.
Figure 6B:
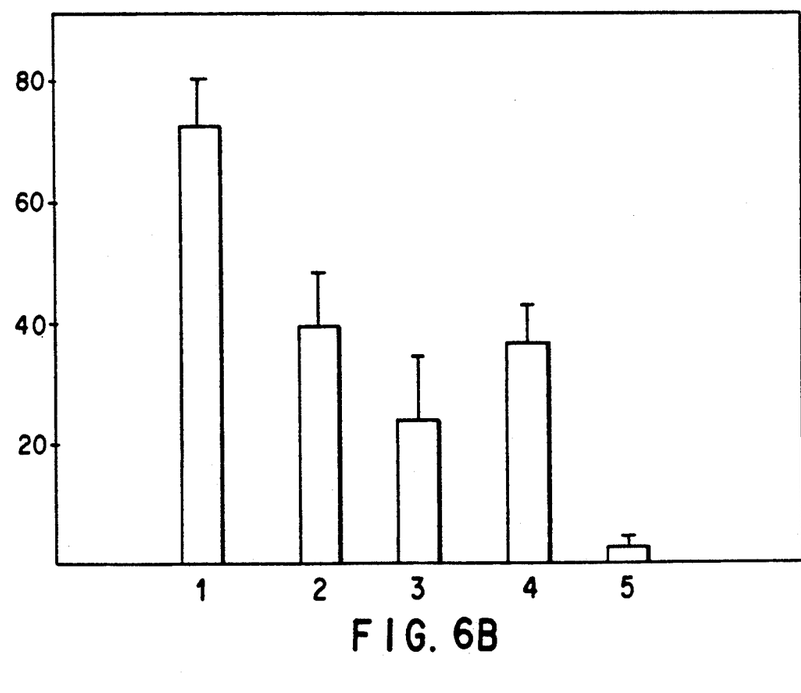
Figure 6C:
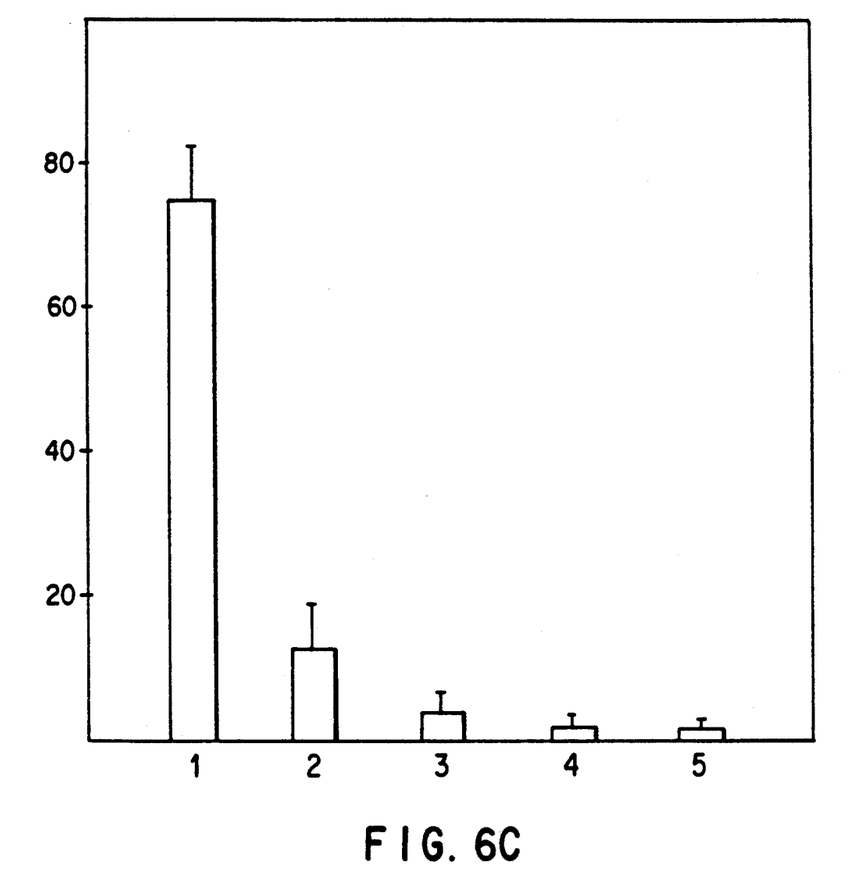

The effectiveness of TMS in vivo is summarized in the graphs comprising FIG. 6. BL6 cells were injected into mice and metastatic deposits in the lung were assessed after various treatments including route and timing of administration. TMS is effective in suppressing lung colonization and tumor development irrespective of route or timing although early treatment is preferred and repeated treatment is more effective. As revealed in the data summarized in panels B and C, there is a distinct dose responsiveness of lung tumor colonization to TMS.

Figure 7A:
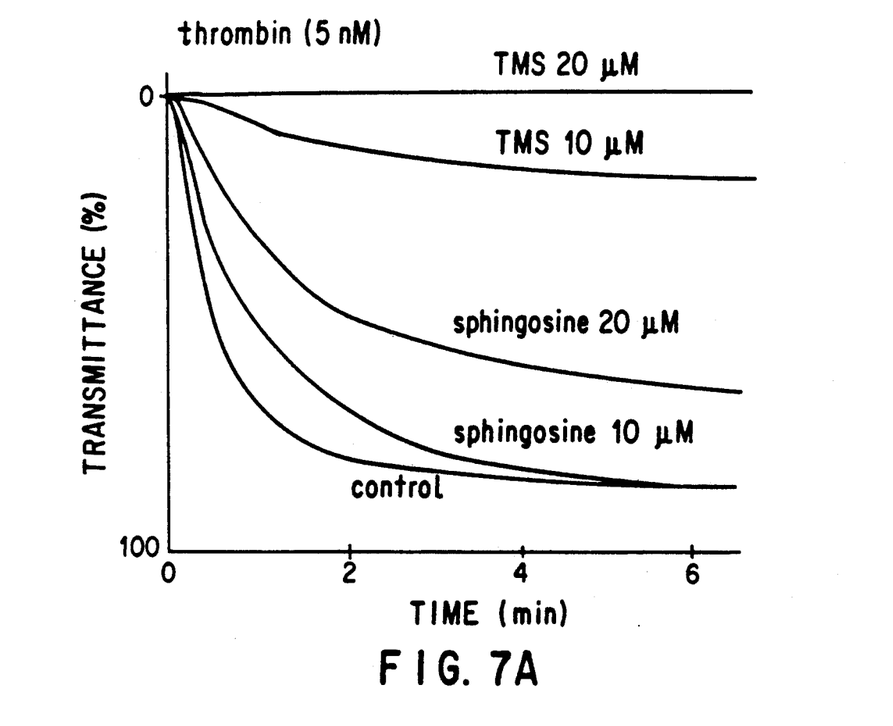
Figure 7B:
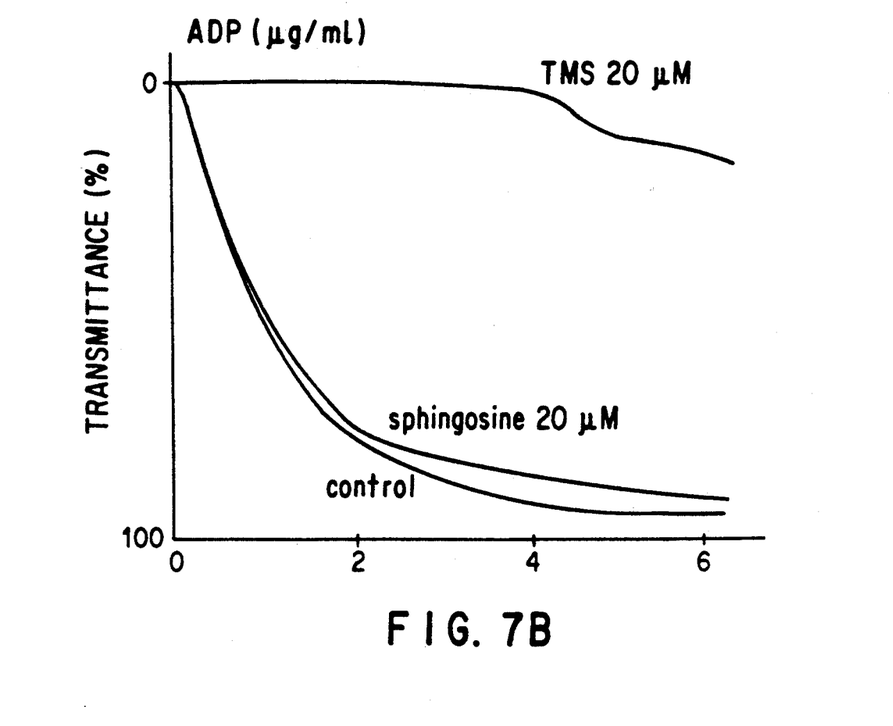
Figure 8:
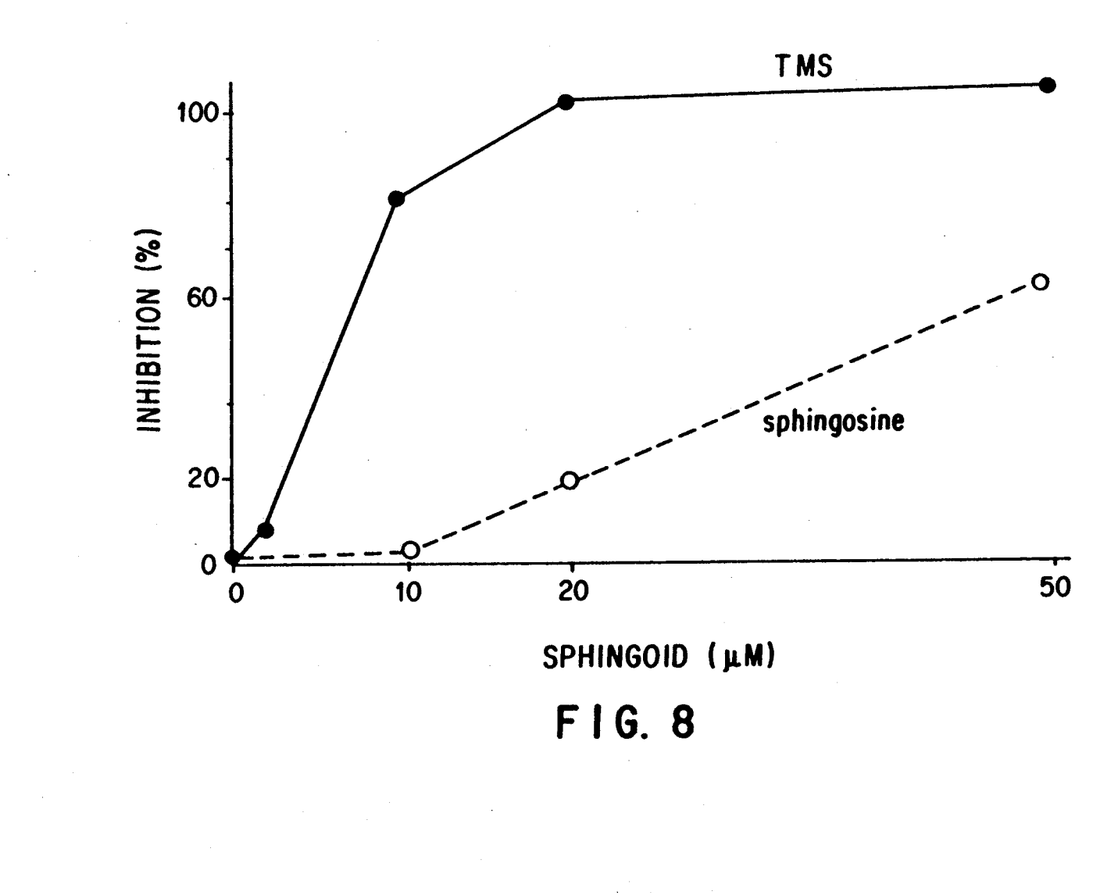
FIG. 8 depicts further the dose response of platelet aggregation by sphingoid. Aggregation of the platelets was induced with 10 nM $\gamma$-thrombin.

Another aspect of TMS is the profound effect it has on platelet aggregation. As presented in the data summarized in FIGS. 7 and 8, TMS inhibited platelet aggregation in a dose-responsive fashion.

Figure 9:
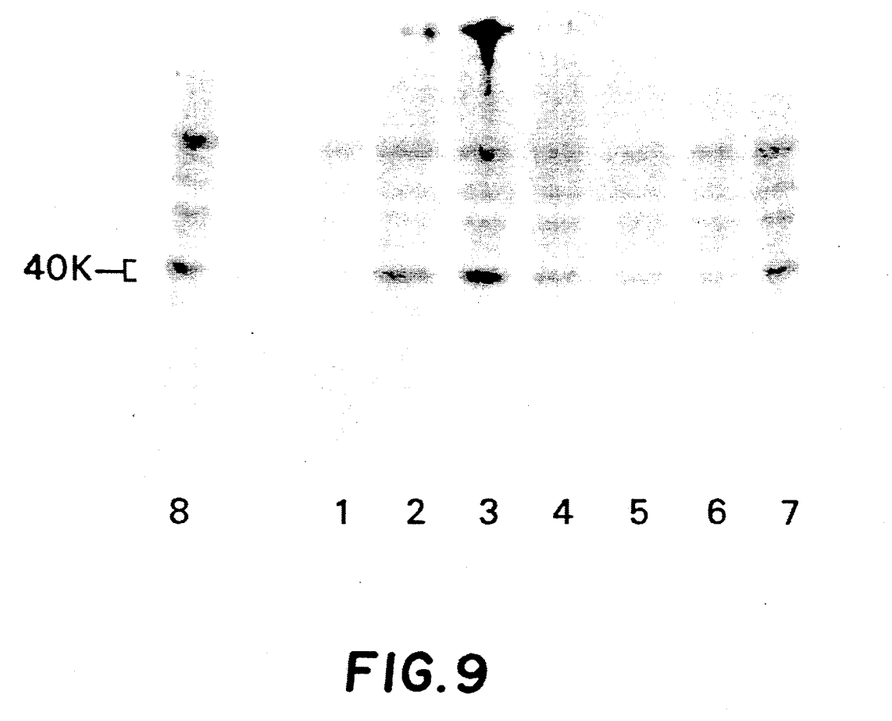

Upon thrombin stimulation, a 40 kD platelet protein is phosphorylated. As noted in FIG. 9, TMS exposure inhibits phosphorylation of the 40 kD platelet protein. While not wanting to be bound by their statement, the inventors believe that absence of phosphorylated 40 kD protein prevents platelet aggregation.

Figure 10:
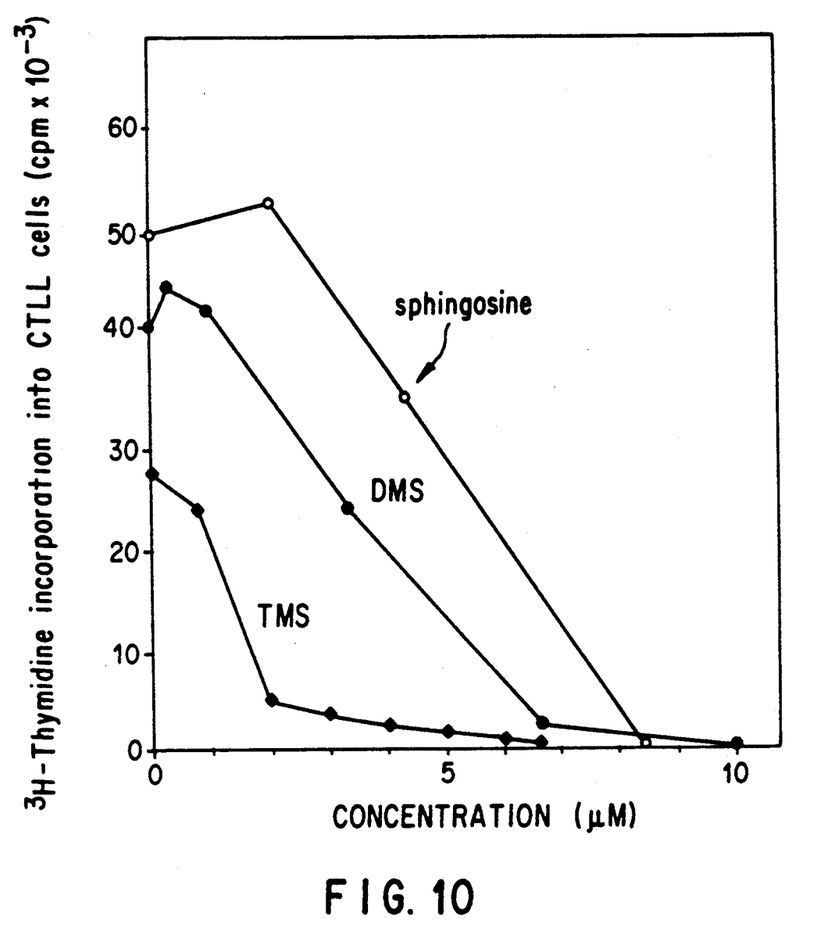
FIG. 10 depicts the effect of sphingosine derivatives on mouse T-cell line CTLL. Each point is the mean of three replicates. In the figure DMS represents N,N-dimethylsphingosine and TMS represents N,N,N-trimethylophingosine.

The utility of TMS is not limited to the suppression of malignant cell growth. Inflammation is characterized in part by a proliferation of lymphoid and myeloid cells. Generally the proliferation serves a beneficial purpose, such as sequestration of foreign antigen or enhancement of restorative capabilities following an insult, but at times can occur abnormally, for example as a result of an autoimmune dysfunction. Thus TMS has utility in controlling cell proliferation of apparently normal cells. Mouse CTLL-2 cells (ATCC No. TIB 214), a T lymphocyte cell line, were plated at $1.5 \times 10^4$ cells per well and exposed to test substances. Cell proliferation was monitored by thymidine incorporation. The data of several experiments are summarized in FIG. 10. TMS was significantly more effective in suppressing CTLL-2 cell growth.

Accordingly, the present invention provides a method for inhibiting growth of human and animal cells comprising the step of exposing said human or animal cells to a cell growth inhibiting amount of N,N,N-trimethylsphingosine or pharmaceutically acceptable salts thereof.

The present invention further provides a medicaments and treatments for inhibiting growth in human and animal cells and aggregation of human and animal platelets comprising:
(1) a therapeutically effective amount of N,N,N-trimethylsphingosine or pharmaceutically acceptable salts thereof; and
(2) a pharmaceutically acceptable carrier, diluent or excipient.

The medicaments and methods are applicable both for in vitro and in vivo applications. Specific uses include treatment of malignancies, benign tumorous growths, inflammation, other manifestations of immune system dysfunction and when the immune system inappropriately or excessively responds to a stimulus.

The medicament comprises an effective amount of TMS and a pharmaceutically acceptable carrier, diluent or excipient. The effective amount of TMS can be determined using art-recognized methods, such as by establishing dose-response curves in suitable animal models, such as described herein or in non-human primates, and extrapolating to human; extrapolating from suitable in vitro data, for example as described herein; or by determining effectiveness in clinical trials.

Suitable doses of medicaments of the instant invention depend upon the particular medical application, such as the severity of the disease, the weight of the individual, age of the individual half-life in circulation etc., and can be determined readily by the skilled artisan. The number of doses, daily dosage and course of treatment may vary from individual to individual.

TMS can be administered in a variety of ways such as orally, parenterally and topically. Suitable pharmaceutically acceptable carriers, diluents, or excipients for the medicaments of the instant invention depend upon the particular medical use of the medicament and can be determined readily by the skilled artisan.

The medicament can take a variety of forms such as tablets, capsules, bulk or unit dose powders or granules; may be contained within liposomes; or may be formulated into solutions, emulsions, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. The artisan can configure the appropriate formulation comprising TMS and seeking guidance from numerous authorities and references such as "Goodman & Gilman's The Pharmaceutical Basis of Therapeutics" (6th ed., Goodman et al., eds., MacMillan Publ. Co., NY, 1980).

In body sites that are characterized by continual cell growth or require cell growth inhibition because of dysfunction and are relatively inaccessible, TMS can be administered in a suitable fashion to assure effective local concentrations. For example, TMS may be injected in a depot or adjuvant, carried in a surgically situated implant or reservoir that slowly releases a fixed amount of TMS over a period of time or may be complexed to recognition molecules with the capability of binding to the site presenting with abnormal cell growth. An example of such a contemplated scenario is a recognition molecule that is an antibody with binding specificity for a bone marrow specific antigen wherein said marrow-specific antibody is complexed to TMS, said complex administered to a patient with leukemia.

While the invention has been described in detail and with reference to certain embodiments thereof, it would be apparent to one skilled in the art that various changes and modifications can be made without departing from the spirit and scope thereof.

What is claimed is:

1. A method of synthesizing N,N,N-trimethylsphingosine comprising the steps of:
   (a) treating N,N-dimethylsphingosine with iodomethane to produce a precipitate; and
   (b) extracting said precipitate with chloroform.

2. The method of claim 1 wherein said N,N-dimethylsphingosine is synthesized by a process comprising the steps of:
   (a) treating sphingenine with formaldehyde;
   (b) exposing said treated sphingenine to sodium cyanoborohydride and excess methanol to produce N,N-dimethylsphingosine; and
   (c) extracting said N,N-dimethylsphingosine with chloroform.

* * * * *

UNITED STATES PATENT AND TRADEMARK OFFICE
CERTIFICATE OF CORRECTION

PATENT NO. : 5,248,824
DATED : September 28, 1993
INVENTOR(S) : Igarashi et al.

It is certified that error appears in the above-indentified patent and that said Letters Patent is hereby corrected as shown below:

Column 1, line 18, change "dehydroxy" to --dihydroxy--;
        line 29, change "$C_6$" to --$C_\alpha$--;
        line 31, after "Megidish" insert --&--;
        line 61, change "C1" to --C2--;
        line 63, after "group", delete ----;
Column 2, line 18 and 24, both occurrences, change "trimethylaphingosine" to --trimethylsphingosine--;
Column 3, line 63, change "T" to --δ--.
Column 4, line 11, change "electrophotecti-" to --electrophoreti---;
        line 26, change "thylosphingosine" to --thylsphingosine--.
        line 37, change "D- or, L-" to --D- or L-,or--;
        line 44, change "golipide" to --golipids--;
        line 49, change "$NAH_2PO_3$" to --$NaCNBH_3$--; and
        line 64, change "$NaBH_3$-CN" to --$NaCNBH_3$--.
Column 5, line 8, change "MEOH" to --MeOH--.
Column 6, line 45, change "ehtanol" to --ethanol--;
        line 59, change "f or" to --for--; and
        line 64, change "NAOH" to --NaOH--.
Column 7, line 16, after "6323" delete ","; and
        line 67, delete "a".
Column 8, line 26, after individual, second occurrence, insert --,--.

Signed and Sealed this

Thirteenth Day of August, 1996

Attest:

BRUCE LEHMAN

*Attesting Officer*      *Commissioner of Patents and Trademarks*